United States Patent [19]

Vida

[11] 4,087,529

[45] May 2, 1978

[54] THERAPEUTIC COMPOSITION CONTAINING AN N-MONO (ALKOXY-METHYL) PHENOBARBITAL AND A METHOD OF TREATING CONVULSIONS THEREWITH

[75] Inventor: Julius A. Vida, Greenwich, Conn.

[73] Assignee: Bristol-Myers Company, New York, N.Y.

[21] Appl. No.: 781,027

[22] Filed: Mar. 24, 1977

Related U.S. Application Data

[60] Division of Ser. No. 616,498, Sep. 24, 1975, Pat. No. 4,054,565, which is a division of Ser. No. 434,385, Jan. 18, 1974, Pat. No. 3,948,896, which is a continuation-in-part of Ser. No. 336,424, Feb. 28, 1973, abandoned.

[51] Int. Cl.² .......................................... A61K 31/515
[52] U.S. Cl. .................................................... 424/254
[58] Field of Search ......................................... 424/254

[56] References Cited

U.S. PATENT DOCUMENTS

| | | | |
|---|---|---|---|
| 3,904,627 | 9/1975 | Vida et al. | 424/254 |
| 3,919,427 | 11/1975 | Vida et al. | 424/254 |
| 3,948,896 | 4/1976 | Vida | 424/254 |

*Primary Examiner*—Paul M. Coughlan, Jr.
*Attorney, Agent, or Firm*—Irving Holtzman; Morton S. Simon; David J. Mugford

[57] ABSTRACT

N-mono(alkoxymethyl)phenobarbitals wherein the alkoxy group has 1 to 4 carbon atoms are disclosed. The compounds are prepared by reacting the dialkali metal salt of thiophenobarbital with chloromethyl alkyl ether followed by treating the resultant N,S-bis(alkoxymethyl)thiophenobarbital with an oxidizing agent. The compounds are useful as anti-convulsant agents.

6 Claims, No Drawings

THERAPEUTIC COMPOSITION CONTAINING AN N-MONO (ALKOXY-METHYL) PHENOBARBITAL AND A METHOD OF TREATING CONVULSIONS THEREWITH

This application is a division of Application Ser. No. 616,498 filed Sept. 24, 1975 now U.S. Pat. No. 4,054,565 which in turn is a division of Application Ser. No. 434,385 filed Jan. 18, 1974 now U.S. Pat. No. 3,948,896 which in turn is a continuation-in-part of Application Ser. No. 336,424 filed Feb. 28, 1973 now abandoned.

This invention relates to N-mono(alkoxymethyl)-phenobarbitals, to a process therefor, to therapeutic compositions containing same and to their use as agents for treating convulsions and seizures in warm-blooded animals.

Recently a series of N,N'-bis(alkoxymethyl)-phenobarbitals has been prepared and described in the art. C. M. Samour, J. F. Reinhard and J. A. Vida in J. Medicinal Chemistry 14, p. 187 (1971), reported that alkoxymethylation of phenobarbital in the presence of two equivalents of base provided N,N'-bis(alkoxymethyl)phenobarbital in nearly quantitative yield. When only one equivalent of base was used, N,N'-bis(alkoxymethyl)phenobarbital was obtained in 50% yield, with 50% of unreacted starting material being recovered. In neither reaction was any mono-alkoxymethylated product obtained.

Now it has been found in accordance with this invention that N-mono(alkoxymethyl)phenobarbitals having the following formula wherein R is an alkyl group having from 1 to 4 carbon atoms can be provided:

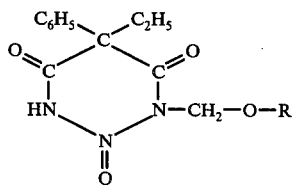

More in detail, the process of this invention comprises reacting the dialkali metal salt of thiophenobarbital with chloromethyl alkyl ether and treating the resultant N,S-bis(alkoxymethyl)thiophenobarbital with an oxidizing agent in accordance with the following general reaction scheme wherein R is as previously described and M represents an alkali metal such as sodium, potassium, lithium, etc.

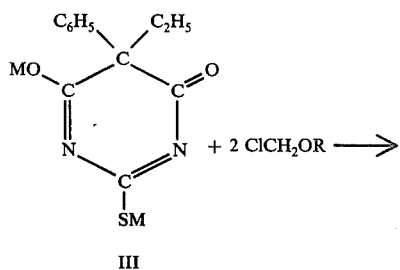

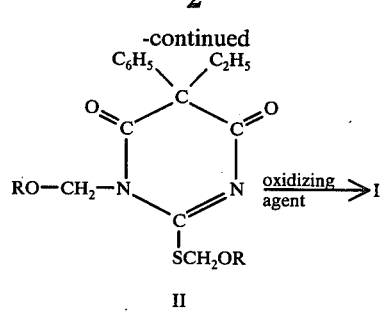

The dialkali metal salt III which is readily obtained from thiophenobarbital and two equivalents of an alkali metal source, is reacted with a chloromethyl alkyl ether such as chloromethyl methyl ether, chloromethyl isopropyl ether, chloromethyl t-butyl ether, chloromethyl butyl ether, etc. The alkali metal source can be finely powdered sodium, sodium amalgam, sodamide, sodium hydride, lithium hydride, potassium hydride, potassium t-butoxide, etc. The reaction is carried out in the presence of an inert solvent. Suitable solvents include dimethyl formamide, dimethyl acetamide, dimethyl sulfoxide, N-methylpyrrolidone, acetonitrile, diglyme, etc. Preferably, the dialkali metal salt III is prepared in such a diluent and reacted in situ with the chloromethyl alkyl ether.

The reaction to provide the N,S-bis(alkoxymethyl)-thiophenobarbital II proceeds over a wide temperature range, conveniently from $-15°$ C up to the boiling point of the solvent.

Compound II is then treated with an oxidizing agent to obtain the desired N-mono(alkoxymethyl)phenobarbital I. Exemplificative oxidizing agents include mixtures of hydrogen peroxide with acids such as acetic acid, trifluoroacetic acid, etc.; peracids such as peracetic acid, trifluoroperoxyacetic acid, perbenzoic acid, performic acid; chromic acid in acetic acid; aqueous potassium permanganate; etc. The oxidation proceeds over a wide temperature range, preferably from about $-10°$ C to about $100°$ C. The resultant N-mono(alkoxymethyl)phenobarbitals I are obtained in high yields and are isolated from the reaction mixture by any appropriate technique such as extraction, etc.

For this application, the compounds can be formulated for oral or parenteral administration according to conventional techniques. Effectiveness and toxicity of these compounds is such that each dosage unit can contain from 5 to 500 mg. of active material. Compositions for oral administration can be solid or liquid and can take the form of syrups, isotonic solutions, tablets, capsules etc. Suitable solid physiologically acceptable carriers include lactose, magnesium stearate, sucrose, talc, stearic acid, gelatin, polyvinyl pyrrolidone etc. Exemplary liquid physiologically acceptable carriers are peanut oil, olive oil, sesame oil and water. Furthermore the carrier may include a time delay material such as glyceryl monostearate or glyceryl distearate, alone or in combination with a wax.

If a solid carrier is used, the preparation can be tableted, placed in a hard gelatin capsule or in the form of a troche or lozenge. The amount of solid carrier will vary widely but preferably will be from about 25 mg. to about 1 gm. If a liquid carrier is used, the preparation may be in the form of a soft gelatin capsule, placed in an ampule or in a liquid suspension.

For parenteral administration, the carrier or excipient may be a sterile, parenterally acceptable liquid; e.g., water or a parenterally acceptable oil; e.g., arachis oil contained in ampules.

While any of the above compositions are efficacious, preferred are tablets for oral administration.

The procedures employed for demonstrating efficacy of the compounds as set forth in the following examples were as follows.

All tests, with the exceptions noted, were conducted on albino male mice (Charles River strain); the dosage consisted of the active agent suspended in 10% aqueous acacia and was administered orally unless otherwise indicated.

Acute oral toxicity was determined in the conventional manner. The results were expressed as $LD_{50}$, the dose required to produce death in 50% of the animals treated.

The time of peak anticonvulsant activity was determined by administering dosages of various sizes to a group of animals and administering a maximal electroshock to the animals at intervals thereafter by supplying 60 ma. current through a corneal electrode for 0.2 second. Protection was indicated if the animal failed to show the tonic extensor component of the maximal electroshock seizure pattern in unprotected animals. The time of peak effect thus determined was used for all subsequent tests of anticonvulsant activity on the same active agent.

Anticonvulsant effectiveness of each agent was determined against maximal electroshock administered as described above, against a convulsive dose of Metrazol (106.25 mg/kg) injected subcutaneously. In the case of maximal electroshock the criterion for effectiveness was failure to show the tonic extensor component of the seizure pattern; in the case of Metrazol, the failure to show clonic convulsive seizures indicated effectiveness.

Hypnotic activity or depression of the central nervous system as indicated by loss of the righting reflex (onset of sleep) was either absent or weak in the case of any dosage of any of the compounds of the present invention less than a lethal dose. Phenobarbital itself on the other hand did exhibit potent hypnotic activity using the foregoing criterion, as is well known.

The following examples will serve to illustrate the practice of this invention.

EXAMPLE 1

In a 50 ml. flask equipped with a stirrer and condenser, 2.48 g. (0.01 mole) of 2-thiophenobarbital was dissolved in 10 ml. dimethylformamide. To the solution 200 mg. (0.025 mole) of lithium hydride was added. The resulting suspension was stirred at room temperature for 15 minutes. To the suspension 3.2 g. (0.04 mole) of chloromethyl methyl ether was added over a period of 30 minutes. The temperature of the reaction mixture was kept below 50° C during the addition of chloromethyl methyl ether. The reaction mixture was stirred at room temperature for one hour, then poured into a separatory funnel which contained 100 g. of a mixture of ice and water. The product was extracted several times with ethyl acetate. The ethyl acetate solutions were combined and washed with water, dried over sodium sulfate and evaporated to dryness. The oily residue was purified by column chromatography on silica gel. Elution with benzene provided 3.2 g. (95% of the theoretical yield) of pure N,S-bis(methoxymethyl)-2-thiophenobarbital.

Analysis. — Calc'd for $C_{16}H_{20}O_4N_2S$: C, 57.14; H, 5.95; N, 8.33; S, 9.53 Found: C, 57.49; H, 5.76 N, 8.44; S, 9.68

When tested for anticonvulsant activity against maximal electroshock, it exhibited peak activity approximately two hours after the administration of the drug, exhibiting an $ED_{50}$ greater than 100 mg/kg. The compound did not exhibit hypnotic activity at a dose of 100 mg/kg.

In a 500 ml. flask equipped with a stirrer and condenser, 5.00 g. (0.015 mole) of the N,S-bis(methoxymethyl)-2-thiophenobarbital was dissolved in 50 ml. trifluoroacetic acid. To the solution 15 ml. of a 37% aqueous solution of hydrogen peroxide was added slowly, drop by drop. The solution was stirred for 20 hours at a temperature of 40°–50° C. Then the solution was poured into a separatory funnel which contained 500 g. of a mixture of ice and water. The product was extracted several times with ethyl acetate. The ethyl acetate solutions were combined and washed with water, dried over sodium sulfate and evaporated to dryness. The oily residue was purified by column chromatography on silica gel. Elution with a solvent mixture containing 90% benzene - 10% ethyl acetate provided 3.7 g. (90% of the theoretical yield) of N-(methoxymethyl)-phenobarbital, an oily solid.

Analysis. — Calc'd for $C_{14}H_{16}O_4N_2$: C, 60.86; H, 5.84; N, 10.14 Found: C, 61.01; H, 5.91; N, 9.95

The compound exhibited anticonvulsant activity against maximal electroshock, having a time of peak activity approximately two hours after administration of dose. The effective dose ($ED_{50}$) was found to be about 22.5 mg/kg. When tested against Metrazol, the effective dose ($ED_{50}$) was 3.9 mg/kg. The acute oral toxicity ($LD_{50}$) was $> 250 < 500$ mg/kg and the hypnotic activity ($HD_{50}$)$> 0 < 500$ mg/kg.

EXAMPLE 2

In a 50 ml. flask equipped with a stirrer and condenser, 2.48 g. (0.01 mole) of 2-thiophenobarbital was dissolved in 10 ml. dimethyl formamide. To the solution 200 mg. (0.025 mole) of lithium hydride was added and the resulting suspension was stirred at room temperature for 15 minutes. To the suspension 4.9 g. (0.04 mole) of chloromethyl n-butyl ether was added and the remainder of the procedure was carried out exactly as described in Example 1, obtaining 3.95 g. (94% of the theoretical yield) of N,S-bis(n-butoxymethyl)-2-thiophenobarbital.

Analysis. — Calc'd for $C_{22}H_{32}O_4N_2S$: C, 62.82; H, 7.67; N, 6.66; S, 7.63 Found: C, 62.46; H, 7.79; N, 6.84; S, 7.93

When tested for anticonvulsant activity against maximal electroshock, it exhibited peak activity approximately two hours after the administration of the drug, having an approximate $ED_{50}$ of 50 mg/kg. The compound was devoid of hypnotic activity up to doses of 1000 mg/kg.

In a 500 ml. flask equipped with a stirrer and condenser, 3.8 g. of the N,S-bis(n-butoxymethyl)-2-thiophenobarbital was dissolved in a mixture of 5 ml. trifluoroacetic acid and 50 ml. acetic acid. To the solution 50 ml. of a 37% aqueous solution of hydrogen peroxide was added slowly, drop by drop and the remainder of the procedure was carried out exactly as described in Example 1 obtaining 2.54 g. (88% of the theoretical yield) of N-(n-butoxymethyl)-phenobarbital, an oil.

Analysis — Calc'd for $C_{17}H_{22}O_4N_2$: C, 64.13; H, 6.97; N, 8.80 Found: C, 64.19; H, 6.89 N, 8.70

The compound exhibited anticonvulsant activity against Metrazol, having a time of peak activity approximately one hour after administration of the dose. The effective dose ($ED_{50}$) was found to be approximately 62.5 mg/kg. The compound also exhibited anticonvulsant activity against maximal electroshock, having a time of peak activity approximately one hour after administration of the dose. The effective dose ($ED_{50}$) was found to be approximately 125 mg/kg. The compound was devoid of hypnotic activity up to doses of 750 mg/kg. The acute oral toxicity ($LD_{50}$) was found to be 750 mg/kg.

EXAMPLE 3

The amount of 6.0 g. (.025 mole) of sodium hydride was added to a solution of 24.8 g. (0.1 mole) of 5-ethyl-5-phenyl-2-thiobarbituric acid in 100 ml. dimethyl formamide. The resulting suspension was stirred at room temperature. To the suspension 20.8 g. (0.26 mole) of chloromethyl methyl ether was added over a period of 40 minutes. During the addition of the chloromethyl methyl ether, the temperature of the reaction mixture was kept below 50° C. After stirring the reaction mixture for 90 minutes, it was poured onto 500 g. of a mixture of ice and water. Then the product was extracted with ethyl acetate and solvent evaporated to provide 32.0 g. (96% of theoretical yield) of N,S-bis(methoxymethyl)-2-thiophenobarbital. Elution with 95% benzene and 5% ethyl acetate provided pure products.

To a cooled solution of 31.0 g. of the N,S-bis(methoxymethyl)-2-thiophenobarbital in 500 ml. trifluoroacetic acid was added. dropwise, 150 ml. of a 37% aqueous solution of hydrogen peroxide. The solution was stirred at 45°–50° C for 3 hours and then poured onto 2000 g. of a mixture of ice and water. The product was extracted with ethyl acetate and the solvent evaporated to provide a residue that was purified by column chromatography on silica gel. Elution with a mixture containing 90% benzene and 10% ethyl acetate provided 22.5 g. (90% of the theoretical yield) of N-(methoxymethyl)-phenobarbital.

Analysis. — Calc'd for $C_{14}H_{16}N_2O_4$: C, 60.86; H, 5.84; N, 10.14, Found; C, 61.00; H, 5.96; N, 10.00.

What is claimed is:

1. A therapeutic composition for the treatment of convulsions in warm-blooded animals which comprises a physiologically acceptable carrier and an anticonvulsant effective amount of an N-mono(alkoxymethyl)-phenobarbital in which the alkoxy group has from 1 to 4 carbon atoms.

2. The composition of claim 1 wherein said N-mono(alkoxymethyl)phenobarbital is N-methoxymethyl phenobarbital.

3. The composition of claim 1 wherein said N-mono(alkoxymethyl)phenobarbital is N-butoxymethyl phenobarbital.

4. A method for treating convulsions in a warm-blooded animal which comprises administering to said animal an anticonvulsant effective amount of the N-mono(alkoxymethyl)phenobarbital composition of claim 1.

5. The method of claim 4 wherein said N-mono(alkoxymethyl) phenobarbital is N-methoxymethyl phenobarbital.

6. The method of claim 4 wherein said N-mono(alkoxymethyl) phenobarbital is N-butoxymethyl phenobarbital.

* * * * *